(12) United States Patent
Ramaseshan et al.

(10) Patent No.: US 10,711,208 B2
(45) Date of Patent: Jul. 14, 2020

(54) PROCESS SCHEME FOR THE PRODUCTION OF OPTIMAL QUALITY DISTILLATE FOR OLEFIN PRODUCTION

(71) Applicant: Saudi Arabian Oil Company, Dhahran (SA)

(72) Inventors: Vinod Ramaseshan, Ras Tanura (SA); Bruce R. Beadle, Dhahran (SA); Marcus J. Killingworth, Dhahran (SA); Abdulaziz S. Al-Ghamdi, Ad Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 218 days.

(21) Appl. No.: 15/628,086

(22) Filed: Jun. 20, 2017

(65) Prior Publication Data

US 2018/0362863 A1    Dec. 20, 2018

(51) Int. Cl.
*C10G 67/04* (2006.01)
*C10G 45/50* (2006.01)
(Continued)

(52) U.S. Cl.
CPC ..... *C10G 67/0436* (2013.01); *B01D 53/1468* (2013.01); *C10G 7/06* (2013.01);
(Continued)

(58) Field of Classification Search
CPC ........ C10G 21/02; C10G 21/12; C10G 21/14; C10G 21/20; C10G 21/22; C10G 21/28;
(Continued)

(56) References Cited

U.S. PATENT DOCUMENTS

| 2,846,358 A | 3/1956 | Bieber et al. |
| 3,204,006 A | 8/1965 | Broughton |

(Continued)

FOREIGN PATENT DOCUMENTS

| GB | 1286383 | 8/1972 |
| WO | 2018094333 A1 | 5/2018 |

OTHER PUBLICATIONS

Nagy, Gabor, et al., "Hydrodearomatization of Gas Oil Fractions on PT-PD/USY Catalyst" Petroleum & Coal ISSN 1337-7027, 49 (1), 2007, pp. 24-32.

(Continued)

*Primary Examiner* — Renee Robinson
(74) *Attorney, Agent, or Firm* — Bracewell LLP; Constance G. Rhebergen; Brian H. Tompkins

(57) ABSTRACT

Systems and processes for hydrotreating, splitting, and extracting a gasoil feed to produce a saturate-rich feedstock for olefin pyrolysis are provided. A gasoil feed is provided to a hydrotreating section to produce an ultralow sulfur distillate (ULSD) stream. The ULSD stream is provided to a splitter section to produce a light distillate stream and a heavy bottom stream. The light distillate stream is provided to an extraction section to produce an aromatic-rich extract phase and a saturate-rich raffinate phase. The raffinate phase is mixed with the heavy bottom stream to produce an olefin pyrolysis feedstock having a reduced BMCI as compared to the gasoil feed stream and the ULSD stream.

16 Claims, 2 Drawing Sheets

(51) Int. Cl.

| | |
|---|---|
| *C10G 21/02* | (2006.01) |
| *C10G 65/04* | (2006.01) |
| *C10G 7/06* | (2006.01) |
| *B01D 53/14* | (2006.01) |
| *C10G 45/44* | (2006.01) |
| *C10G 9/00* | (2006.01) |
| *C10G 45/60* | (2006.01) |
| *C10G 69/06* | (2006.01) |
| *C07D 211/76* | (2006.01) |
| *C07C 317/08* | (2006.01) |
| *B01D 11/00* | (2006.01) |
| *C10G 21/22* | (2006.01) |
| *C10G 21/20* | (2006.01) |
| *C10G 21/14* | (2006.01) |

(52) U.S. Cl.
CPC ............... *C10G 9/00* (2013.01); *C10G 45/44* (2013.01); *C10G 45/50* (2013.01); *C10G 45/60* (2013.01); *C10G 65/04* (2013.01); *C10G 67/0418* (2013.01); *C10G 69/06* (2013.01); *B01D 11/00* (2013.01); *B01J 2231/641* (2013.01); *C07C 317/08* (2013.01); *C07D 211/76* (2013.01); *C10G 21/02* (2013.01); *C10G 21/14* (2013.01); *C10G 21/20* (2013.01); *C10G 21/22* (2013.01); *C10G 2300/1059* (2013.01); *C10G 2400/06* (2013.01); *C10G 2400/20* (2013.01)

(58) Field of Classification Search
CPC ........ C10G 45/08; C10G 45/50; C10G 67/04; C10G 67/0409; C10G 67/0418; C10G 67/0436; C10G 2300/1048; C10G 2300/202; C10G 2400/06
See application file for complete search history.

(56) References Cited

U.S. PATENT DOCUMENTS

| | | |
|---|---|---|
| 3,472,909 A | 10/1969 | Raymond |
| 3,696,023 A | 10/1972 | Koch |
| 3,788,976 A | 1/1974 | Kirk |
| 4,113,607 A | 9/1978 | Miller |
| 4,170,544 A | 10/1979 | Miller |
| 4,260,474 A * | 4/1981 | Wernicke ............... C10G 69/06 208/57 |
| 4,764,266 A | 8/1988 | Chen et al. |
| 5,021,143 A | 6/1991 | Franckowiak et al. |
| 5,925,234 A * | 7/1999 | Morel .................... C10G 67/00 208/96 |
| 8,778,170 B2 | 7/2014 | Long et al. |
| 8,894,839 B2 | 11/2014 | Ramaseshan |
| 9,556,389 B2 | 1/2017 | Koseoglu |
| 2004/0182750 A1 | 9/2004 | Khanna et al. |
| 2004/0245147 A1 | 12/2004 | Boucher Ashe |
| 2013/0081976 A1 | 4/2013 | Heraud et al. |
| 2015/0166435 A1 | 6/2015 | Serban et al. |
| 2016/0281008 A1 | 9/2016 | Kumar et al. |
| 2016/0369188 A1 | 12/2016 | Housmans et al. |

OTHER PUBLICATIONS

Nahas, Robert S., "VGO pretreatment can have a 1-year payout" Oil & Gas Journal, (c) 1980 PennWell Publishing Company Sep. 1, 1980, pp. 1-8.

Rhoe, Andrei, et al., "VGO hydrogenation reaps benefits in olefin production" (c) 1981 PennWell Publishing Company, Oil & Gas Journal Jan. 26, 1981, pp. 1-9.

International Search Report and Written Opinion for related PCT application PCT/US2018/038151 International Filing Date Jun. 19, 2018; Report dated Sep. 26, 2018; pp. 1-14.

* cited by examiner

PROCESS SCHEME FOR THE PRODUCTION OF OPTIMAL QUALITY DISTILLATE FOR OLEFIN PRODUCTION

BACKGROUND

Field of the Disclosure

The present disclosure generally relates to the processing of hydrocarbon fluids. More specifically, embodiments of the disclosure relate to the processing of gasoil to maximize olefin production.

Description of the Related Art

Olefins such as an ethylene may be produced from crude oil. Ethylene in particular is a widely used industrial chemical that may be used for the production of polyethylene, ethylene oxide, several other chemicals, and in other applications. Existing processes for ethylene production use an ethane feedstock to produce ethylene via pyrolysis. As the feedstock becomes heavier, more reactions occur to produce ethylene. For example, longer chain paraffins are cracked down to ethane before being dehydrogenated. The aromatics in such heavier feedstocks are unreactive, and the resulting ethylene yield is lower. Commensurately, the by-product yield of propylene, butylene, pyrolysis gasoline (referred to as "pygas" and rich in C5-C9 aromatics) and pyrolysis fuel oil (referred to as "PFO" and including C10+ hydrocarbons) increases. Thus, as the feedstock becomes heavier and more aromatic, the ethylene yield decreases and heavy product yield increases. The pygas and PFO byproducts are of lower value than the olefin products. Moreover, heavier feedstocks require a more complex ethylene unit and a resulting greater capital expenditure.

SUMMARY

When ethane is not available for ethylene production but liquid feeds are available, existing production processes typically integrate with a fuels refinery, aromatics complex or both to process the less-selective feedstocks and pyrolysis byproducts. Various prior art examples of such processing are described supra.

When processing heavy oil, existing refineries process vacuum gasoil through a hydrocracking or deep hydrotreating unit in which the "hydrowax" (deeply hydrotreated or hydrocracked fractionator bottom) is fed to an olefin pyrolysis unit with produced distillate (produced by cracking of the vacuum gasoil). The overall yield of ethylene from the hydrowax in such processes may be in the range of about 25 weight (wt) % to about 27 wt %.

When using only atmospheric gasoil as a feedstock, existing refineries use desulfurization followed by aromatic saturation in a two-stage hydroprocessing unit. Although such techniques may result in a relatively greater ethylene yield, the distillate still contains an equilibrium quantity of monoaromatics. Chen et al. (U.S. Pat. No. 4,764,266) discusses an integrated hydroprocessing scheme for production of premium quality distillate. This integrated hydroprocessing scheme is a combination of mild hydrocracking/hydrotreating followed by a second stage aromatic saturation unit with a noble metal catalyst. Such hydro-dearomatization (aromatic saturation) of gasoil fractions typically requires a moderate to high hydrogen partial pressure, low Liquid Hourly Space Velocity (LHSV), and a high hydrogenating metal function catalyst.

One process for removing aromatic compounds is a slurry treatment of gasoil or kerosene feedstock with activated carbon. A process using this method is described by Haskell et al. (U.S. Pat. No. 4,634,516) as a feed preparation step prior to an olefin pyrolysis unit.

When lighter feedstocks (feedstocks typically in the naphtha and kerosene ranges) are processed, the objective is to treat alkyl aromatic-containing hydrocarbons mixtures in the presence of hydrogen for the removal of alkyl radicals from the aromatic component (referred to as "hydrodealkylation"). Broughton (U.S. Pat. No. 3,204,006) describes the separation of the resulting aromatic hydrocarbons from the hydrodealkylation product via adsorption.

In another related field within a refinery, kerosene range components (that is, having a boiling range of 125° C. to 310° C.) are typically dearomatized using solvent extraction to produce an odor free "dual purpose kerosene" (DPK) with a relatively high smoke point which can be used as jet fuel and as heating oil. The Edeleanu process of using liquid sulfur dioxide ($SO_2$) as a solvent to dearomatize kerosene has been used for over a century. The limitations imposed by the use of liquid sulfur dioxide (e.g., cryogenic operating conditions and a highly corrosive properties) has resulted in the development of alternate solvents for such dearomatization. Conventional liquid-liquid extraction using pure or modified dimethylsulfoxide, dimethylfomamide, n-methyl pyrolidone (as described, for example, in U.S. Publication No. 2004/0182750 and French Patent Nos 1,421,273 and 1,424,225) have been practiced commercially.

Additionally, existing refineries have used a combination of hydrotreatment followed by extraction for maximizing gasoline octane. Franckowiak et al. (U.S. Pat. No. 5,021,143) describes a method of fractionation and extraction of hydrocarbons to obtain a cut of increased octane index and kerosene of improved smoke point.

Embodiments of the disclosure are generally directed to systems and processes for hydrotreating, splitting, and extraction of a gasoil feed to produce a saturate-rich feedstock for maximizing olefin production that is lean in aromatics and with a reduced Bureau of Mines Correlation Index (BMCI) as compared to the gasoil feed. The secondary product is an aromatic-rich stream that may be used for aromatics production.

In one embodiment, a method of producing a feedstock for olefin pyrolysis is provided. The method includes hydrotreating a gasoil feed with a hydrotreating catalyst in the presence of hydrogen to produce an ultralow sulfur distillate (ULSD) stream having less than 10 parts-per-million weight (ppmw) sulfur and less than 10 ppmw nitrogen and separating the ULSD stream into a light distillate stream and a heavy bottom stream, such that aromatics in the light distillate stream are at least 50% by weight monoaromatics and aromatics in the heavy bottom stream are no more than 15% by weight monoaromatics. The method also includes extracting an extract phase and a raffinate phase from the light distillate stream, the raffinate phase having at least 50% by weight saturated hydrocarbons and no more than 15% by weight aromatics and mixing the raffinate phase with the heavy bottom stream to produce the feedstock for olefin pyrolysis.

In some embodiments, a Bureau of Mines Correlation Index (BMCI) of the feedstock for olefin pyrolysis is less than the BMCI of the gasoil feed and the BMCI of the ULSD stream. In some embodiments, the light distillate stream has a true boiling point (TPB) in the range of 140° C. to about 300° C. In some embodiments, the heavy bottom stream has a true boiling point (TPB) in the range of 300° C. to about 400° C. In some embodiments, the gasoil feed has a true boiling point (TPB) in the range of about 140° C. to about 400° C. In some embodiments, the hydrotreating is performed at a temperature in the range of 200° C. to 450° C. and a pressure in the range of 34 barg to 100 barg. In some embodiments, the hydrotreating catalyst is a heterogeneous fixed bed catalyst includes at least one Group VIII metal and at least one Group VIB metal. In some embodiments, the at least one Group VIII metal is selected from the group consisting of iron, cobalt and nickel and the at least one Group VIB metal is selected from the group consisting of molybdenum and tungsten. In some embodiments, separating the ULSD stream into a light distillate stream and a heavy bottom stream includes separating the ULSD stream via a tray distillation column. In some embodiments, the stripping is performed at a temperature in the range of about 40° C. to 400° C. and a pressure in the range of about 0.05 barg to about 20 barg. In some embodiments, extracting the extract phase and the raffinate phase from the light distillate stream is performed in an extraction section having a liquid-liquid extraction (LLE) column, secondary re-extract column, an extract and raffinate wash column, a distillation column, and a solvent recovery column. In some embodiments, extracting the extract phase and the raffinate phase via the liquid-liquid extraction (LLE) column includes using a first solvent and a second solvent. In some embodiments, the first solvent is N-Methyl-2-pyrrolidone (NMP) or dimethyl sulfoxide (DMSO). In some embodiments, the second solvent is paraffinic light naphtha or C6 and C7 hydrocarbons. In some embodiments, the extract phase includes at least 50% by weight aromatics.

In another embodiment, a system is provide that includes a hydrotreating section operable to hydrotreat a gasoil feed with a hydrotreating catalyst in the presence of hydrogen to produce an ultralow sulfur distillate (ULSD) stream having less than 10 parts-per-million weight (ppmw) sulfur and less than 10 ppmw nitrogen and a separation section operable to separate the ULSD stream into a light distillate stream and a heavy bottom stream, such that aromatics in the light distillate stream includes at least 50% by weight monoaromatics and the aromatics in the heavy bottom stream includes no more than 15% by weight monoaromatics. The system also includes an extraction section operable to extract an extract phase and a raffinate phase from the light distillate stream, the raffinate phase having at least 50% by weight saturated hydrocarbons and no more than 15% by weight aromatics.

In some embodiments, the light distillate stream has a true boiling point (TPB) in the range of 140° C. to about 300° C. In some embodiments, the heavy bottom stream has a true boiling point (TPB) in the range of 300° C. to about 400° C. In some embodiments, the system includes a mixing apparatus operable to mix the raffinate phase with the heavy bottom stream to produce the feedstock for olefin pyrolysis, such that a Bureau of Mines Correlation Index (BMCI) of the feedstock for olefin pyrolysis is less than the BMCI of the gasoil feed and the BMCI of the ULSD stream. IN some embodiments, the gasoil feed has a true boiling point (TPB) in the range of about 140° C. to about 400° C. In some embodiments, the hydrotreating catalyst is a heterogeneous fixed bed catalyst having at least one Group VIII metal and at least one Group VIB metal. In some embodiments, the at least one Group VIII metal is selected from the group consisting of iron, cobalt and nickel and at least one Group VIB metal is selected from the group consisting of molybdenum and tungsten. In some embodiments, the extraction section includes a liquid-liquid extraction (LLE) column, secondary re-extract column, an extract and raffinate wash column, a distillation column, and a solvent recovery column. In some embodiments, the liquid-liquid extraction (LLE) column includes a first solvent and a second solvent. In some embodiments, the first solvent is N-Methyl-2-pyrrolidone (NMP) or dimethyl sulfoxide (DMSO). In some embodiments, the second solvent is paraffinic light naphtha or C6 and C7 hydrocarbons. In some embodiments, the extract phase includes at least 50% by weight aromatics.

In another embodiment, a method of processing hydrocarbons is provided. The method includes providing a gasoil feed to a hydrotreating section to produce an ultralow sulfur distillate (ULSD) stream, the ultralow sulfur distillate stream having less than 10 parts-per-million weight (ppmw) sulfur and less than 10 ppmw nitrogen and providing the ULSD stream to a splitter section to produce a light distillate stream and a heavy bottom stream, such that the aromatics in the light distillate stream includes at least 50% by weight monoaromatics and the aromatics in the heavy bottom stream includes no more than 15% by weight monoaromatics. The method further includes providing the light distillate stream to an extraction section to produce an extract phase and a raffinate phase, the raffinate phase having at least 50% by weight saturated hydrocarbons and no more than 15% by weight aromatics, and obtaining a feed stream for olefin pyrolysis, the feed stream having the raffinate phase and the heavy bottom stream. In some embodiments, a Bureau of Mines Correlation Index (BMCI) of the feedstock for olefin pyrolysis is less than the BMCI of the gasoil feed and the BMCI of the ULSD stream. In some embodiments, the gasoil feed has a true boiling point (TPB) in the range of about 140° C. to about 400° C. In some embodiments, the hydrotreating catalyst is a heterogeneous fixed bed catalyst having at least one Group VIII metal and at least one Group VIB metal. In some embodiments, the extract phase includes at least 50% by weight aromatics.

DETAILED DESCRIPTION

Figure 1:
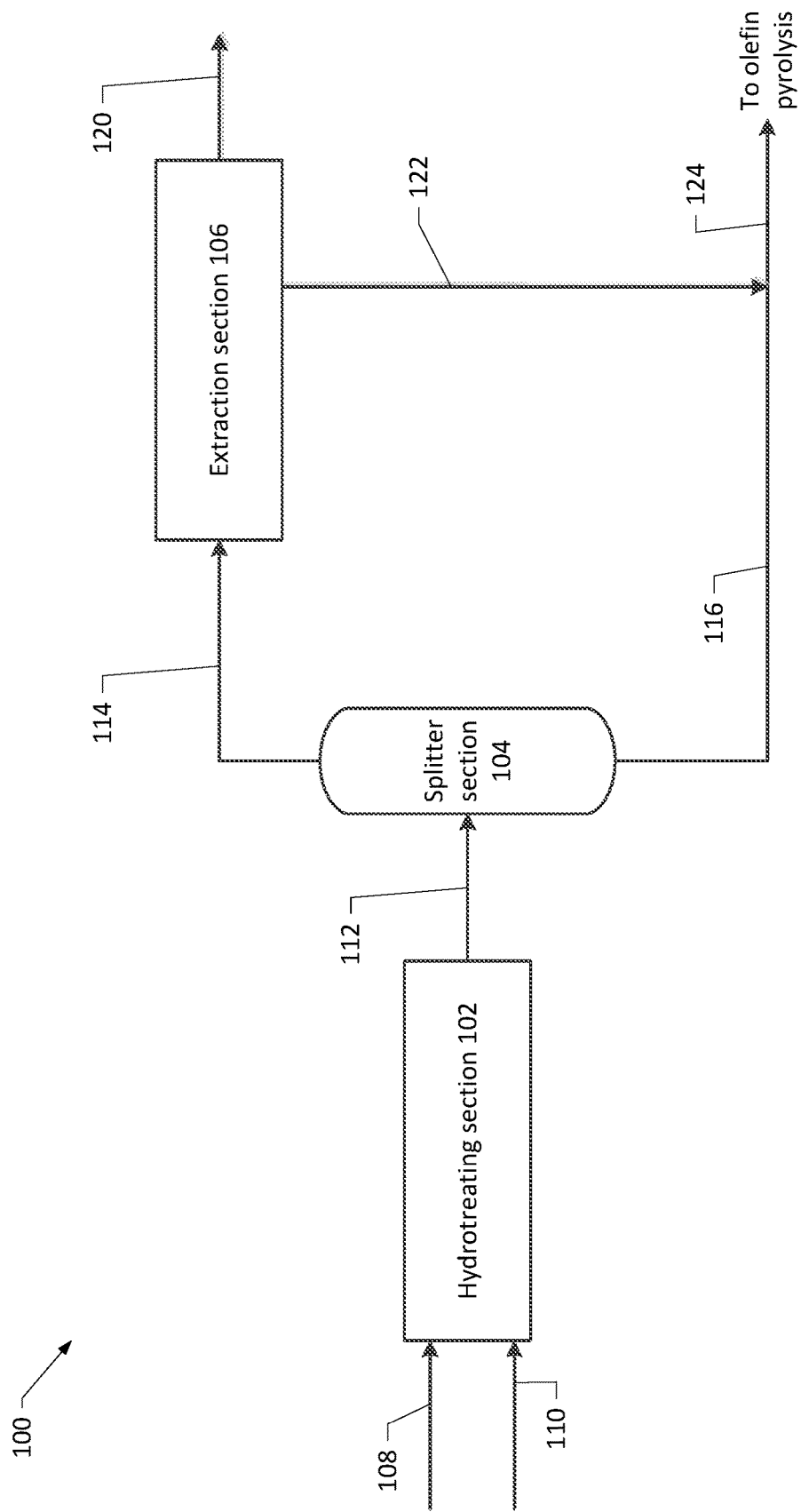
FIG. 1 is a block diagram of a system for hydrotreating, separating, and extracting of a gasoil/distillate fraction to produce a feedstock for olefin pyrolysis in accordance with embodiments of the disclosure.

The present disclosure will now be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

As used herein, the terms "stream" or "main stream" may include various hydrocarbon molecules, such as straight chain, branched, or cyclical alkanes, alkenes, alkadienes, alkynes and aromatics and may, in some embodiments, include other substances such as gases and impurities. As used herein, the terms "stream" or "main stream" may also include aromatic and nonaromatic compounds. 8

As used, the term "zone" or "section" may refer to an area that includes one or more equipment items and may, in some embodiments, include or one or more subzones or subsections. In some embodiments, equipment items may include reactors, reactor vessels, heaters, exchangers, pipes, pumps, compressors, controllers and various combinations thereof. Additionally, an equipment item, such as a vessel, a fractionation column, an extraction column, may further include one or more zones or subzones.

As used herein, the term "rich" refers to an amount of at least about 50% by mole, weight, or volume of a compound or class of compounds in a stream. In some embodiments, the term "rich" may refer to an amount of at least about 70% by mole, weight, or volume of a compound or class of compounds in a stream.

As used herein, the term "lean" may refer to an amount of no more than generally about 15% by mole, weight, or volume of a compound or class of compounds in a stream. In some embodiments, the term "lean" may refer to an amount of at least about 10% by mole, weight, or volume of a compound or class of compounds in a stream.

As used herein, the term "gasoil" (also referred to as "gasoil/distillate") refers to a hydrocarbon stream having a true boiling point (TBP) in the range of about 140° C. to about 400° C. and derived from an atmospheric column from a pipestill, a thermal cracking unit, a fluid catalytic cracking unit, a residual hydroprocessing unit, or any combination thereof.

As used herein, the term "true boiling point" (TPB) refers to measurements from a standard batch distillation test (for example, as described in ASTM D2892-16, Standard Test Method for Distillation of Crude Petroleum (15-Theoretical Plate Column), ASTM International, West Conshohocken, Pa., 2016) for crude oil or crude oil fractions to determine the quantity of the petroleum cuts within tan oil.

As used herein, the term "BMCI" refers to the Bureau of Mines Correlation Index that provides a measurement of the aromaticity and saturate content of a hydrocarbon mixture and its suitability for production of olefins via pyrolysis.

Embodiments of the disclosure include systems and processes for hydrotreating, separating, and extracting a gasoil feed to produce a saturate-rich feedstock lean in aromatic hydrocarbons and having a decreased BMCI suitable for maximizing olefin production from pyrolysis. Such embodiments include a hydrotreating section that that receives a gasoil feed and produces an ultralow sulfur distillate (ULSD) having less than 10 parts-per-million by weight (ppmw) sulfur, less than 10 parts-per-million by weight (ppmw) nitrogen, and maximized aromatic saturation such that most of the aromatics remaining in the ULSD products are monoaromatics. Embodiments of the disclosure include a splitter section that receives the ULSD stream from the hydrotreating section and splits the hydrotreated gasoil into a light distillate stream and a heavy bottom stream. Embodiments also include an extraction section that receives the light distillate stream from the splitter section and produces an aromatic-rich extract phase and a saturate-rich raffinate phase.

The hydrotreating of the gasoil feed may be performed in the presence of hydrogen over a hydrotreating catalyst and at a temperature in the range of 200° C. to 450° C. and a pressure in the range of 34 barg to 100 barg. In some embodiments, the catalyst is a heterogeneous fixed bed catalyst that includes at least one Group VIII metal and at least one Group VIB metal. In some embodiments, the Group VIII metal is selected from the group consisting of iron, cobalt and nickel. In some embodiments, the Group VIB metal is selected from the group consisting of molybdenum and tungsten. In some embodiments, the Group VIII metal in present in an amount in the range of about 2 wt % to about 20 wt % by weight. In some embodiments, the Group VIB metal is present in the amount in the range of about 1 wt % to about 25% wt %. In some embodiments, the at least one Group VIII metal and at least one Group VIB metal may be disposed on a support material, such as alumina with silica or alumina without silica. In other embodiments, other support materials and promotors may be used.

The splitter section may include a tray distillation column that receives the ULSD stream from the hydrotreating section and produces a light distillate stream rich in aromatics and a heavy bottom stream lean in aromatics. In some embodiments, the tray distillation column may be a stream stripped column or a furnace assisted column.

The extraction section may include a liquid-liquid extraction column, a secondary re-extract column, an extract and raffinate wash column, a distillation column, and a solvent recovery column. The solvent extraction section extracts the aromatics from the light distillate stream received from the splitter section to produce an extract phase rich in aromatics and a raffinate phase rich in saturated hydrocarbons. The extraction section may be a dual solvent extraction using a primary solvent and a secondary solvent. The extract phase may be routed to fuel oil blending or used as a flux oil component.

The feedstock for olefin pyrolysis is be produced by mixing the raffinate phase from the extraction section and the heavy bottom stream from the splitter section. The mixed stream is lean in aromatics and has a lesser BMCI than the gasoil feed or the ULSD produced by the hydrotreating section.

FIG. 1 depicts a system 100 for hydrotreating, splitting, and extracting a gasoil feed to produce a saturate-rich feedstock for olefin pyrolysis in accordance with embodiments of the disclosure. The saturate-rich feedstock may have a reduced BMCI as compared to the gasoil feed to maximize olefin production. As shown in FIG. 1, the system 100 includes a hydrotreating section 102, a splitter section 104, and an extraction section 106.

The hydrotreating section 102 may receive a gasoil feed stream 108 and a hydrogen stream 110 (that is, make-up hydrogen and, in some embodiments, recycle hydrogen from hydrotreating). The gasoil feed stream 108 may include one or more of the following: gasoil from atmospheric distillation of crude oil; thermally cracked gasoil from a coker, thermal cracker, or visbreaker; light cycle oil from fluid catalytic cracking (FCC); and distillates from residue hydroprocessing units. In some embodiments, the gasoil feed stream 108 has a TBP in the range of about 140° C. to about 400° C. The hydrotreating section 102 may saturate the aromatics present in the gasoil feed stream 108 to produce an ultralow sulfur distillate (ULSD). As will be appreciated, the staged saturation of aromatics in the hydrotreating section may produce an ultralow sulfur distillate having maximum aromatic saturation such that the ultralow sulfur distillate stream such that the aromatics remaining the ULSD stream are rich in monoaromatics. For example, in some embodiments, the ULSD stream may include 70 wt % saturates and 30 wt % aromatics, such that the ULSD stream may include 24 wt % monoaromatics and 6 wt % di- and tri-aromatics.

The hydrotreating in the hydrotreating section 102 is performed in the presence of hydrogen and, in some embodiments, the hydrotreating may performed at a temperature in the range of 200° C. to 450° C. and a pressure in the range of 34 barg to 100 barg. In some embodiments, the hydrotreating section may include a heterogeneous fixed bed catalyst. In some embodiments, the catalyst includes at least one Group VIII metal and at least one Group VIB metal. In some embodiments, the Group VIII metal is selected from the group consisting of iron, cobalt and nickel. In some embodiments, the Group VIB metal is selected from the group consisting of molybdenum and tungsten. In some embodiments, the Group VIII metal in present in an amount in the range of about 2 wt % to about 20 wt % by weight. In some embodiments, the Group VIB metal is present in the amount in the range of about 1 wt % to about 25% wt %. In some embodiments, the at least one Group VIII metal and at least one Group VIB metal may be disposed on a support material, such as alumina with silica or alumina without silica. In other embodiments, other support materials and promotors may be used.

As will be appreciated, a specific amount of hydrotreating occurs in the hydrotreating section 102 as the feed stream 108 is passed over the catalyst at the selected hydrogen pressures and temperatures. In some embodiments, the amount of catalyst used per volume of feed and the hydrotreating pressures may be based on the quality of the feed stream and the product stream. In some embodiments, hydrogen may be provided in amounts greater than the stoichiometric amounts (for example, in the range of about 3 to about 4 times greater than the consumed amount) to minimize coking and provide a heat sink for the exothermic hydrotreating reaction. In some embodiments, recycle gas from the hydrotreating section may be subjected to amine gas treatment (that is, amine scrubbing) to remove the hydrogen sulfide (H2S) formed in the reaction.

The hydrotreating section 102 may include a stripping column. After separation and flashing of the reactor effluent from hydrotreating, the reactor effluent may be stripped of the light ends in the stripping column to produce a stabilized full range ultralow sulfur distillate (ULSD) stream 112. The ULSD stream has less than 10 ppmw sulfur and less than 10 ppm. Nitrogen. As noted supra, the aromatics in the ULSD stream are rich in monoaromatics. In some embodiments, the stripping column may be operated at a temperature in the range of about 40° C. to 400° C. and a pressure in the range of about 0.05 barg to about 20 barg.

As shown in FIG. 1, the splitter section 104 may receive the ULSD stream 112 from the hydrotreating section 102. The splitter section 104 splits the ULSD stream 112 into a light distillate stream 114 and a heavy bottom stream 116. By way of example, the light distillate stream 114 may have a TBP in the range of about 140° C. to about 300° C. (also referred to as a kerosene range cut) and the heavy bottom stream 116 may have a TBP in the range of about 300° C. to about 400° C. After splitting of the ULSD stream 112, the light distillate stream includes the majority of the monoaromatics from the ULSD stream 112, such that the aromatics in the light distillate stream are at least 50 wt % monoaromatics, while the heavy bottom stream is lean in the monoaromatics, such that the aromatics in the heavy bottom stream are no more than 15% by weight monoaromatics. As discussed in the disclosure, the heavy bottom stream is used as a component in the olefin pyrolysis feedstock.

The splitter may include a tray distillation column. In some embodiments, the tray distillation column of the splitter section 104 may be operated at a temperature in the range of about 40° C. to 400° C. and a pressure in the range of about 0.05 barg to about 20 barg. In some embodiments, the tray distillation column may be a stream stripped column or a furnace assisted column.

As further shown in FIG. 1, the light distillate stream 114 from the splitter section 104 may be provided to the extraction section 106. The extraction section 106 extracts aromatics from the light distillate stream 114 and produces an extract phase 120 and a raffinate phase 122. The extraction section 106 may be a dual solvent system (that is, a system using a primary solvent and second solvent) and may include a liquid-liquid extraction (LLE) column, a secondary re-extract column, an extract and raffinate wash column, a distillation column, and a solvent recovery column. In some embodiments, the weight ratio of the primary solvent to feed is in the range of about 3:1 to about 5:1. In some embodiments, the primary solvent may be N-Methyl-2-pyrrolidone (NMP), dimethyl sulfoxide (DMSO), or other suitable commercial solvents mixed with water, glycol, sulfolane, or furfural. In some embodiments, the secondary solvent may be a light hydrocarbon such as paraffinic light naphtha or a C6 and C7 hydrocarbon solvent (for example, a typical C6 and C7 stream readily available in a refinery) with a circulation rate of about 4:1 by volume to the extract phase.

In some embodiments, the extraction and raffinate wash column may be operated at a temperature in the range of about 30° C. to about 80° C. In some embodiments, the secondary solvent recovery from the extract phase may be performed at a temperature in the range of about 100° C. to about 300° C. and a pressure in the range of about 0.5 barg to about 2 barg. In some embodiments, the primary solvent recovery may be performed at a bottom temperature in the range of about 100° C. to about 180° C. bottom temperature and a pressure in the range of about 0.5 barg to about 2 barg.

The extract phase 120 produced from the extraction section 106 is rich in aromatics and, in some embodiments, may be used as a fuel oil blending component (for example, by routing to a refinery fuel oil pool) or as a flux oil component in further processing, such as heavy oil hydroprocessing.

The raffinate phase 122 produced from the extraction section 106 is rich in saturated hydrocarbons and is used as a component in the olefin pyrolysis feedstock. The raffinate phase 122 may be mixed with the heavy bottom stream 116 from the splitter section 104 to produce a feedstock 124 for olefin pyrolysis. The raffinate phase 122 may be mixed with the heavy bottom stream 116 using a static mixer or a powered mixing apparatus with moving components. The mixer may be, for example, an in-line mixer, a, a t-line mixer, or other suitable mixing apparatus. The feedstock 124 may be provided to an olefin pyrolysis unit. Advantageously, the feedstock 124 has a reduced BMCI and an increased American Petroleum Institute (API) gravity as compared to the gas oil feed stream 108 or the ultralow sulfur product stream 110 from the hydrotreating unit 102. As will be appreciated, the feedstock 124 may be an improved feedstock for optimizing olefin (for example, ethylene) production via pyrolysis as compared to the gasoil feed stream 108 that is heavier and has a greater percentage of aromatics.

Embodiments of the disclosure thus provide for use of gasoil in a hydrotreatment section and omit the use of isomerization units and recycling of isomerization effluent with a bleed to fuel oil. Advantageously, the process described herein can use both straight run and cracked (thermally and catalytically) gasoil fractions and generate a feedstock suitable for pyrolysis.

Figure 2:
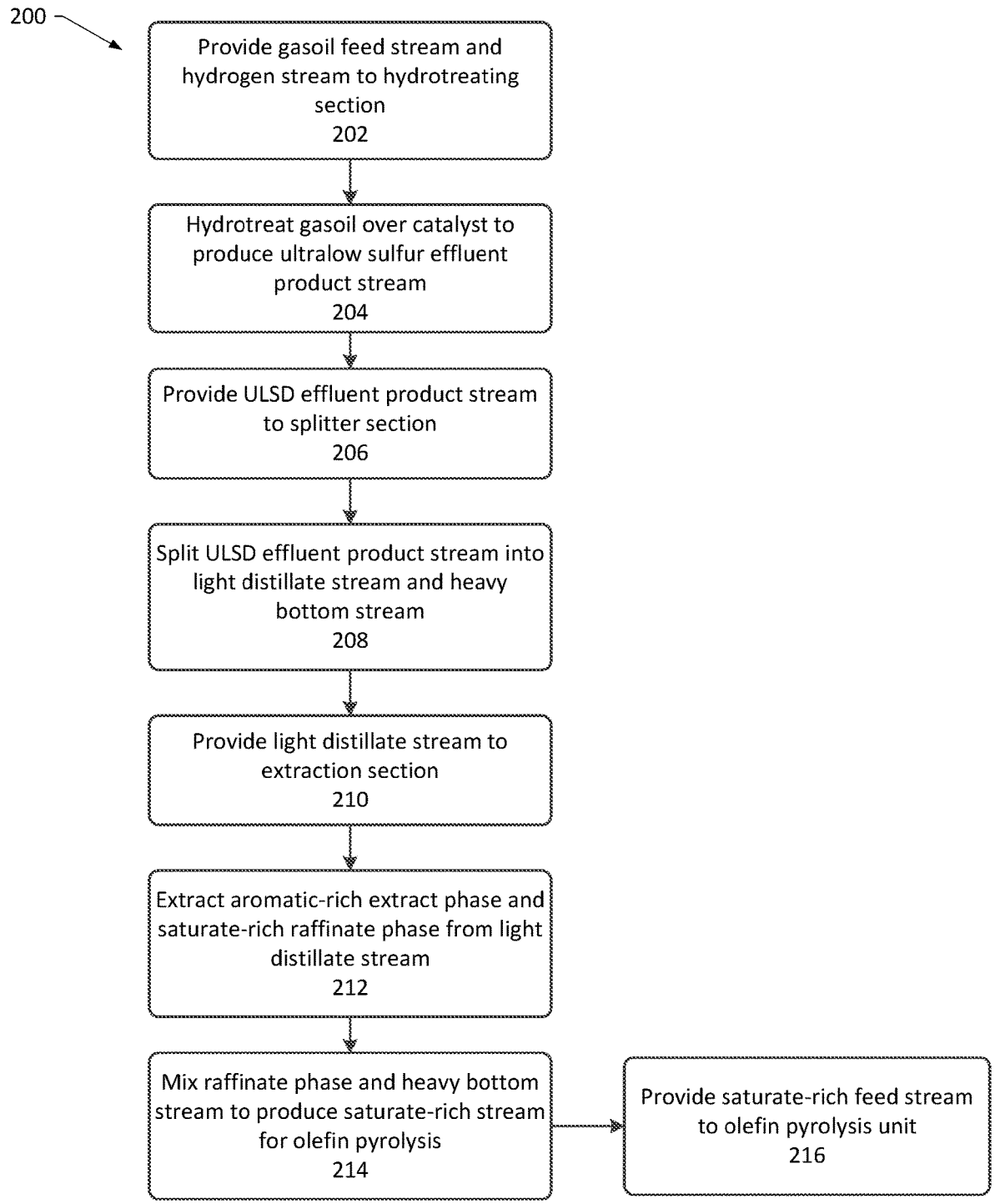
FIG. 2 is a block diagram of a process for hydrotreating, separating, and extracting of a gasoil/distillate fraction to produce a feedstock for olefin pyrolysis in accordance with embodiments of the disclosure.

FIG. 2 is a process 200 for producing a saturate-rich feedstock for olefin pyrolysis in accordance with an embodiment of the disclosure. Initially, a gasoil feed stream and a hydrogen feed stream may be provided to a hydrotreating section (block 202). The hydrogen feed stream may include recycle hydrogen from the hydrotreating process discussed herein and makeup hydrogen. The gasoil feed stream may be provided from other sections in a refinery and, in some embodiments, may have a TBP in the range of 140° C. to 400° C. For example, the gasoil feed stream may include: gasoil from atmospheric distillation of crude oil; thermally cracked gasoil from a coker, thermal cracker, or visbreaker; light cycle oil from fluid catalytic cracking (FCC); and distillates from residue hydroprocessing units.

The gasoil feed stream may be hydrotreated using a hydrotreating catalyst to produce an ultralow sulfur distillate having less than 10 ppmw sulfur and less than 10 ppmw nitrogen (block 204). The ultralow sulfur distillate may have maximum aromatic saturation such that greater than about 95% of the aromatics in the ULSD are monoaromatics. The ULSD stream may be provided to a splitter section (block 206) to split the ULSD stream into a light distillate stream and a heavy distillate stream (block 208). The light distillate stream may have, for example, a TBP in the range of about 140° C. to about 300° C., and a heavy bottom stream, for example, a TBP in the range of about 300° C. to about 400° C. As noted in the disclosure, the splitter section may include a tray distillation column.

The light distillate stream from the splitter section may be provided to an extraction section (block 210). An aromatic-rich extract phase and saturate-rich raffinate phase may be extracted from the light distillate stream (block 212). In some embodiments, for example, the extract phase and raffinate phase may be extracted using a liquid-liquid extraction column, a first solvent, and a second solvent (that is, a dual solvent system). The raffinate phase may be mixed with the heavy bottom stream from the splitter section to produce a feedstock for olefin pyrolysis (block 214) via, for example, an in-line mixer, a, a t-line mixer, or other suitable static or powered mixing apparatus. As discussed in the disclosure, the feedstock produced using the raffinate phase and the heavy bottom stream may have a reduced BMCI and an increased API gravity as compared to the gasoil feed or the ULSD stream produced by hydrotreating the gasoil feed.

The saturate-rich feedstock may then be provided to an olefin pyrolysis unit (block 216). In some embodiments, the aromatic-rich extract phase extracted from the light distillate stream may be used as a fuel oil blending component or a flux oil component in further processing, such as heavy oil hydroprocessing.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method of producing a feedstock for olefin pyrolysis, comprising:
    hydrotreating a gasoil feed with a hydrotreating catalyst in the presence of hydrogen to produce an ultralow sulfur distillate (ULSD) stream comprising less than 10 parts-per-million weight (ppmw) sulfur, less than 10 ppmw nitrogen, and maximum aromatic saturation as compared to the gasoil feed such that greater than 95% by weight of the aromatics in the ULSD stream are monoaromatics;
    separating, via a tray distillation column, the ULSD stream into a light distillate stream and a heavy bottom stream, wherein aromatics in the light distillate stream comprise at least 50% by weight monoaromatics and aromatics in the heavy bottom stream comprise no more than 15% by weight monoaromatics;
    extracting, in an extraction section, an extract phase and a raffinate phase from the light distillate stream, the raffinate phase comprising at least 50% by weight saturated hydrocarbons and no more than 15% by weight aromatics, the extraction section comprising a liquid-liquid extraction (LLE) column, secondary re-extract column, an extract and raffinate wash column, a distillation column, and a solvent recovery column; and
    mixing the raffinate phase with the heavy bottom stream produced from the separation of the ULSD stream to produce the feedstock for olefin pyrolysis, wherein a Bureau of Mines Correlation Index (BMCI) of the feedstock for olefin pyrolysis is less than the BMCI of the gasoil feed and the BMCI of the ULSD stream.

2. The method of claim 1, wherein the light distillate stream has a true boiling point (TPB) in the range of 140° C. to about 300° C.

3. The method of claim 1, wherein the heavy bottom stream has a true boiling point (TPB) in the range of 300° C. to about 400° C.

4. The method of claim 1, wherein the gasoil feed has a true boiling point (TPB) in the range of about 140° C. to about 400° C.

5. The method of claim 1, wherein the hydrotreating is performed at a temperature in the range of 200° C. to 450° C. and a pressure in the range of 34 barg to 100 barg.

6. The method of claim 1, wherein the hydrotreating catalyst is a heterogeneous fixed bed catalyst comprising at least one Group VIII metal and at least one Group VIB metal.

7. The method of claim 6, wherein the at least one Group VIII metal is selected from the group consisting of iron, cobalt and nickel and the at least one Group VIB metal is selected from the group consisting of molybdenum and tungsten.

8. The method of claim 1, comprising stripping a reactor effluent from the hydrotreating using a stripping column, wherein the stripping is performed at a temperature in the range of about 40° C. to 400° C. and a pressure in the range of about 0.05 barg to about 20 barg.

9. The method of claim 1, wherein extracting the extract phase and the raffinate phase via the liquid-liquid extraction (LLE) column comprises using a first solvent and a second solvent.

10. The method of claim 9, wherein the first solvent comprises N-Methyl-2-pyrrolidone (NMP) or dimethyl sulfoxide (DMSO).

11. The method of claim 9, wherein the second solvent comprises paraffinic light naphtha or C6 and C7 hydrocarbons.

12. The method of claim 1, wherein the extract phase comprises at least 50% by weight aromatics.

13. A method of processing hydrocarbons, comprising
providing a gasoil feed to a hydrotreating section with a hydrotreating catalyst to produce an ultralow sulfur distillate (ULSD) stream, the ultralow sulfur distillate stream comprising less than 10 parts-per-million weight (ppmw) sulfur, less than 10 ppmw nitrogen, and maximum aromatic saturation as compared to the gasoil feed such that greater than 95% by weight of the aromatics in the ULSD stream are monoaromatics;
providing the ULSD stream to a splitter section to produce a light distillate stream and a heavy bottom stream, wherein the aromatics in the light distillate stream comprise at least 50% by weight monoaromatics and the aromatics in the heavy bottom stream comprise no more than 15% by weight monoaromatics;
providing the light distillate stream to an extraction section to produce an extract phase and a raffinate phase, the raffinate phase comprising at least 50% by weight saturated hydrocarbons and no more than 15% by weight aromatics, the extraction section comprising a liquid-liquid extraction (LLE) column, secondary re-extract column, an extract and raffinate wash column, a distillation column, and a solvent recovery column; and
obtaining a feed stream for olefin pyrolysis, the feed stream comprising the raffinate phase and the heavy bottom stream produced from the ULSD stream, wherein a Bureau of Mines Correlation Index (BMCI) of the feedstock for olefin pyrolysis is less than the BMCI of the gasoil feed and the BMCI of the ULSD stream.

14. The method of claim 13, wherein the gasoil feed has a true boiling point (TPB) in the range of about 140° C. to about 400° C.

15. The method of claim 13, wherein the hydrotreating catalyst is a heterogeneous fixed bed catalyst comprising at least one Group VIII metal and at least one Group VIB metal.

16. The method of claim 13, wherein the extract phase comprises at least 50% by weight aromatics.

* * * * *